United States Patent
Maijala et al.

(10) Patent No.: US 10,235,500 B2
(45) Date of Patent: Mar. 19, 2019

(54) MONITORING SYSTEM FOR MONITORING SMART PACKAGE CONTENT USE

(75) Inventors: Juha Maijala, Espoo (FI); Raimo Mäkelä, Lohja (FI); Petri Ilkka, Nokia (FI)

(73) Assignee: STORA ENSO OYJ, Helsinki (FI)

( * ) Notice: Subject to any disclaimer, the term of this patent is extended or adjusted under 35 U.S.C. 154(b) by 78 days.

(21) Appl. No.: 13/985,543

(22) PCT Filed: Feb. 14, 2012

(86) PCT No.: PCT/FI2012/050141
§ 371 (c)(1),
(2), (4) Date: Oct. 23, 2013

(87) PCT Pub. No.: WO2012/110700
PCT Pub. Date: Aug. 23, 2012

(65) Prior Publication Data
US 2014/0052467 A1    Feb. 20, 2014

(30) Foreign Application Priority Data
Feb. 15, 2011    (FI) ..................... 20115146

(51) Int. Cl.
*G06F 17/00* (2006.01)
*G06F 19/00* (2018.01)
(Continued)

(52) U.S. Cl.
CPC .......... *G06F 19/3462* (2013.01); *A61J 1/03* (2013.01); *A61J 1/035* (2013.01);
(Continued)

(58) Field of Classification Search
CPC .......................................... G06Q 50/22–50/24
See application file for complete search history.

(56) References Cited

U.S. PATENT DOCUMENTS

| 4,526,474 A | 7/1985 | Simon |
| 6,628,199 B1 | 9/2003 | Ehrensvärd et al. |
(Continued)

FOREIGN PATENT DOCUMENTS

| CA | 2353350 A1 | 1/2003 |
| CN | 1568171 A | 1/2005 |
(Continued)

OTHER PUBLICATIONS

Finish Search Report dated Jan. 26, 2012, issued in FI 20115146.
(Continued)

*Primary Examiner* — Jonathan Ng
(74) *Attorney, Agent, or Firm* — Birch, Stewart, Kolasch & Birch, LLP

(57) ABSTRACT

A monitoring system for monitoring smart package content use, wherein the system comprises a smart package. The smart package in turn comprises removable content units, such as pill type or tablet type or other singly packed objects, as well as most preferably wireless communication elements. The system comprises also database elements with which the smart package can be in communication. In addition, the smart package is adapted to detect said removal of a content unit and to deliver information to said database elements by way of said communication elements, regarding a removal of said content unit. The smart package is identifiable by the database elements on the basis of information delivered by way of said communication elements.

18 Claims, 2 Drawing Sheets

(51) Int. Cl.
*A61J 1/03* (2006.01)
*G09F 3/00* (2006.01)
*G06F 17/30* (2006.01)
*A61J 7/04* (2006.01)

(52) U.S. Cl.
CPC ........ *G06F 17/30368* (2013.01); *G06F 19/00* (2013.01); *G09F 3/00* (2013.01); *G09F 3/0297* (2013.01); *A61J 7/049* (2015.05); *A61J 7/0418* (2015.05); *A61J 7/0436* (2015.05)

(56) References Cited

U.S. PATENT DOCUMENTS

| | | | |
|---|---|---|---|
| 7,170,409 B2 | 1/2007 | Ehrensvärd et al. | |
| 7,178,417 B2 | 2/2007 | Petersen et al. | |
| 2004/0178112 A1* | 9/2004 | Snyder | 206/534 |
| 2005/0037773 A1* | 2/2005 | Holland | G01S 5/0027 |
| | | | 455/456.1 |
| 2005/0162979 A1* | 7/2005 | Ostergaard et al. | 368/10 |
| 2005/0252924 A1 | 11/2005 | Pieper et al. | |
| 2007/0156282 A1* | 7/2007 | Dunn | 700/244 |
| 2007/0204691 A1 | 9/2007 | Bogner et al. | |
| 2008/0149659 A1 | 6/2008 | Dishongh et al. | |
| 2009/0079567 A1* | 3/2009 | Patel | 340/572.1 |
| 2009/0277815 A1 | 11/2009 | Kohl | |
| 2010/0089791 A1 | 4/2010 | Rosenbaum et al. | |
| 2010/0228566 A1* | 9/2010 | Taylor | G06F 19/3462 |
| | | | 705/3 |
| 2013/0088328 A1* | 4/2013 | DiMartino et al. | 340/5.82 |
| 2014/0337867 A1* | 11/2014 | Wilson | 725/9 |

FOREIGN PATENT DOCUMENTS

| | | | |
|---|---|---|---|
| CN | 1761965 A | 4/2006 | |
| CN | 101336868 A | 1/2009 | |
| EP | 2 243 461 A1 | 10/2010 | |
| JP | 2006-520659 A | 9/2006 | |
| WO | WO 02/05039 A1 | 1/2002 | |
| WO | WO 2004/084116 A1 | 9/2004 | |
| WO | WO 2007/043858 A2 | 4/2007 | |
| WO | WO 2010/066456 A1 | 6/2010 | |
| WO | WO 2011054000 A1 * | 5/2011 | .............. A61J 1/035 |

OTHER PUBLICATIONS

PCT/ISA/210—International Search Report dated Jun. 7, 2012, issued in PCT/FI2012/050141.
PCT/ISA/237—Written Opinion of the International Searching Authority dated Jun. 7, 2012, issued in PCT/FI2012/050141.
Extended European Search Report dated Nov. 25, 2016, in European Patent Application No. 12747541.6.
Korean Office Action issued in Korean Application No. 10-2013-7023832 dated Apr. 19, 2017, together with an English translation thereof.

* cited by examiner

MONITORING SYSTEM FOR MONITORING SMART PACKAGE CONTENT USE

The invention relates to monitoring system for monitoring the use of smart package content, as well as to a method for monitoring such use of smart package content.

PRIOR ART

The prior art discloses various arrangements for monitoring the content use of medication packages, such as for example a solution presented by Wachnam et al. in his publication US 2010/0270257, wherein the cap of a medication bottle is provided with detection elements for monitoring opening of the cap. As a result of opening, the cap of a medication bottle is in data communication, for example by way of a modem, with a third party, such as a database.

A problem with such solutions is that medication packages and detection elements presented therein are highly complicated and expensive to use. In addition, they are not very friendly in terms of environment, because, among others, the above-mentioned cap of a medication bottle contains a lot of high standard electronics with its inherent display units and components. As a result, such packages are not recyclable or for example cannot be incinerated among normal combustible waste, because the electronic components used therein contain metals and other environmentally harmful substances. In addition, such packages are inconvenient to carry along, being bulky and requiring for example the use of a modem. Still furthermore, they are quite easily cheated, because the monitoring system is not for example capable of distinguishing whether a medicine was extracted from the medication bottle or whether the cap was merely opened for no particular purpose. In addition, the cap can be opened by someone other than the intended user of the medication container, nor can the system be totally certain as to who actually opened the cap.

SUMMARY

It is one objective of the invention to eliminate or at least alleviate drawbacks related to the prior art. According to one embodiment, the invention pursues to provide a monitoring system as environmentally friendly as possible, which would nevertheless be as simple and convenient as possible to implement, and that a smart medication package used in the system would be recyclable after use.

Another further objective is to provide such a monitoring system, which could make certain at a higher probability that it was definitely the intended user of the medication package who took a medicine, and that the medicine was definitely extracted out of the package. Another objective is that monitoring would be highly transparent for the user and that the system would be easy and inconspicuous to use as one of the normal daily chores.

Some objectives of the invention are achieved by a monitoring system according to claim 1.

The monitoring system of the invention is characterized by what is presented in claim 1 directed to a monitoring system. The method of the invention for monitoring smart package content use is characterized by what is presented in claim 10 directed to a method.

The invention relates to a monitoring system for monitoring smart package content use, wherein the monitoring system comprises:
  a smart package, comprising removable content units, such as pill type or tablet type objects, for example medical pills, as well as most preferably wireless communication elements, and
  database elements.

The smart package is preferably adapted to detect said removal of a content unit and to supply information to said database elements by way of said communication elements regarding the removal of said content unit. Said smart package is identifiable by the database elements on the basis of information delivered thereby over said communication elements. The smart package is capable of transmitting for example a package identifying character string, or optionally its communication elements may transmit a distinct identification message in conjunction with the transmission of information.

According to one embodiment of the invention, the monitoring system has its smart package provided with a specific sensing element for every content unit, such as a pill, for detecting a removal of this particular pill. The smart package is most preferably adapted to detect and identify, by means of said sensing elements, the removal of a specific pill corresponding to a sensing element, and to deliver information, by means of the communication elements, relating to the removal of just this particular pill. The sensing elements are most preferably provided on a backing of the smart package, upon which they can be pressed by methods of printing technology.

According to one embodiment of the invention, the pill-designated sensing element comprises a component, such as a resistor, capacitor, switch, and/or conductor line, which is most preferably fabricated by methods of printing technology. The specific electrical values, such as resistance or capacitance, of at least two printed components present in the backing can be arranged, for example with methods of printing technology, to be different from each other, such that the removal of a pill brings about a change in the structure of a particular component, whereby the removable content unit producing said change can be identified on the basis of the magnitude of a change in the specific electrical value inherent to said component, such as for example a change in resistance or capacitance.

In addition, according to one embodiment of the invention, the communication elements comprise most preferably wireless communication elements, such as a GSM, GPRS or UMTS module, or some other data transfer module functional in a data transfer network, comprising also more recent data transfer technologies, such as 3G and 4G techniques. The smart package may further comprise a smart package identifying element, such as ID information stored in a memory, or for example a SIM card connectable to a data transfer module.

The smart package may additionally comprise also positioning elements, such as for example a GPS receiver, or most preferably a module receiving location data delivered by the cellular information of a mobile communication network. Said module can be for example the above-mentioned data transfer module operating in a mobile communication network, for example a GSM module or the like.

According to one embodiment, the monitoring system has its database elements comprising means for linking the smart package identification information to the smart package user in the database elements. In addition, the system may comprise elements for linking a smart package content use instruction to said smart package identification information in the database element, as well as communication elements for delivering content use relating instructions either to the smart package and/or to some other terminal of the user, such as for example to the user's mobile communicator. In this case, the monitoring system may comprise said terminal unit as well.

According to one embodiment of the invention, the monitoring system's database elements may deliver a reminder instruction for smart package content use, for example in the event that the database elements have not received information from the smart package regarding the smart package content use within a predetermined time frame. It should be noted that the reminder instruction can be delivered either to the smart package or to the user's mobile communicator or to both. The instruction can also be delivered to some other terminal unit, such as for example to a guardian of the medication package user or to a party looking after his/her health, or to an insurance company.

According to one embodiment, the smart package may comprise communication elements for receiving information from the database elements, such as for example for receiving a reminder instruction. The smart package may additionally comprise an attention getter, such as a led component or a sound producing element, by way of which it can produce a reminder to the user for smart package content use on the basis of instruction information received thereby from the database elements.

According to one embodiment of the invention, the monitoring system is capable of comparing location data of both the smart package and the user's other terminal unit, such as a mobile communicator, on the basis of information received thereby from these or from base stations of these. The system may produce for example an alarm in the event that said pieces of location data deviate from each other more than what has been prescribed, especially at a time when, according to the smart package content use instruction, some contents of the smart package should have been removed from said smart package. In particular, an alarm may be triggered by a situation in which a pill was taken from the smart package at a certain location, but the user or his/her mobile communicator was located at this particular moment at least a predetermined distance away from said location of the smart package. The alarm can be for example a notice or request type alarm to the user and/or to some third party, such as caretaking staff, a guardian, or an insurance company.

Specifically, an exemplary method of the invention comprises storing identification information in the database elements regarding the system's smart package, such as for example information about a SIM card included in the smart package and/or other package identifying information. In addition, in the database elements can be stored information for using said smart package content, such as for example a medical prescription along with its dosage instructions and time attributes, according to which time intervals the content should be used as per instruction. The information regarding a smart package content use can be linked with said smart package identification information. By way of communication elements, it is possible to deliver information from said smart package to said database elements, regarding for example the identification of a smart package or a communication module included therein, as well as the removal of a pill, whereby said smart package can be identified by the database elements on the basis of information it has supplied by way of said communication elements, such as on the basis of the ID information of a package or the information of a SIM card included in the module, such as a GSM module, present in the package.

The backing or the smart package of the invention comprises preferably also a power source for supplying electric power to said components of the package. In addition, it comprises a data processing medium, such as a microcircuit, for measuring electrical changes in the backing. Said data processing medium can be adapted to identify also said removed object on the basis of a specific electrical change brought about by said removed object in one of the electrical lines or circuits of said backing or smart package.

It should be noted that the smart package used in the monitoring system, or at least its backing which has pill identifying elements and components, is most preferably a fiber- or plastic-based backing, comprising cardboard or paper or the like fiber-based material. It should particularly be noted that, according to one preferred embodiment, the backing comprises a docking unit for docking said data transfer elements, such as a GSM module or the like, to the backing for example for the duration of medication package use, whereby, after the medication package use, the data transfer elements can be disengaged from the package for connecting the same for example to a new package, and the spent package can be recycled for example along with recyclable board, or incinerated. The docking unit can be fabricated from the same recyclable and environmentally sound material as the smart package or its backing as well, and its conductor lines can be constructed by methods of printing technology similar to those used for printing its other components as well.

DESCRIPTION OF FIGURES

Preferred embodiments of the invention will be described in the following segment slightly more precisely with reference to the accompanying figures, in which.

DETAILED DESCRIPTION OF FIGURES

Figure 1:
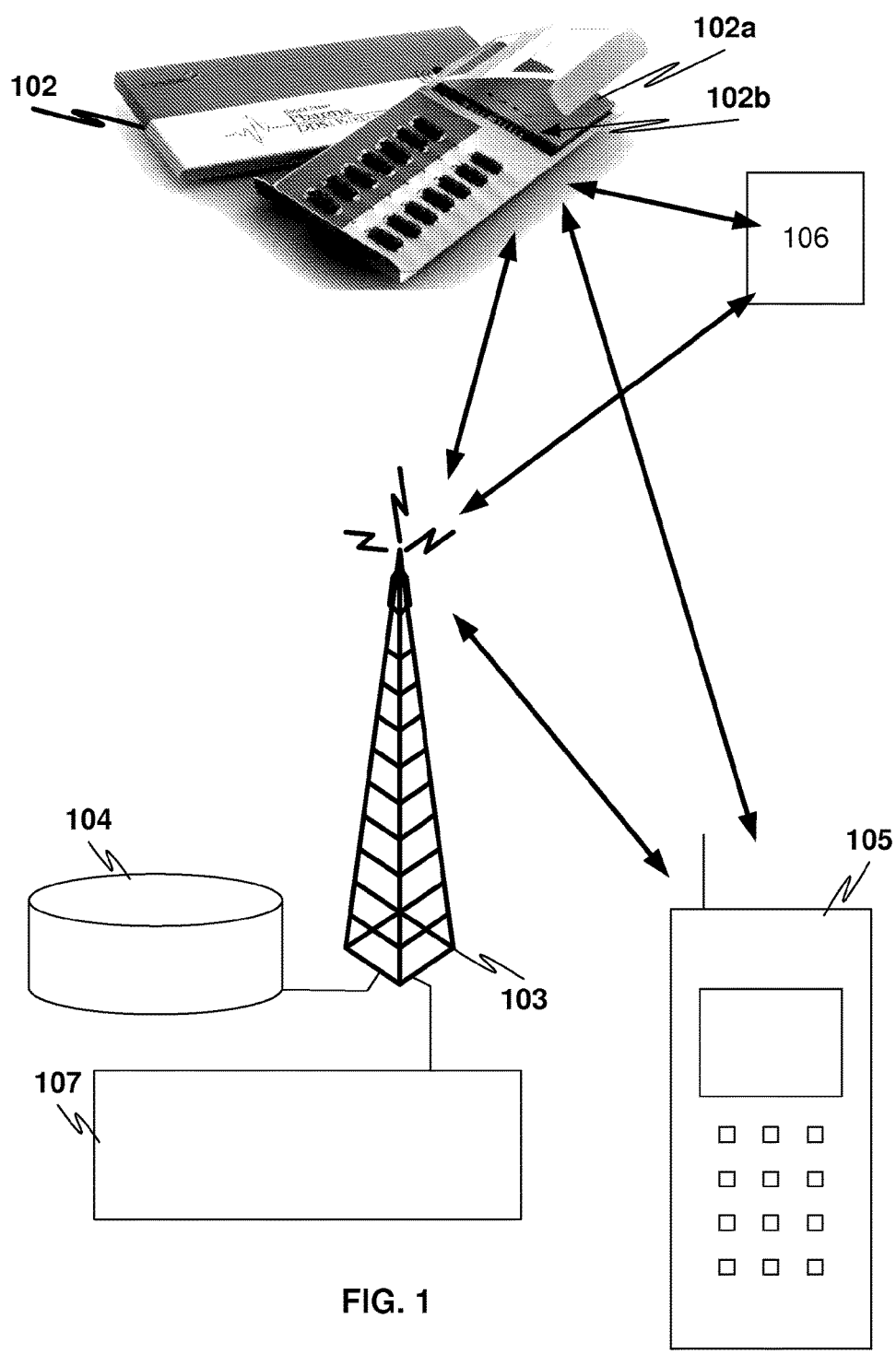
FIG. 1 shows, according to one preferred embodiment of the invention, one exemplary monitoring arrangement.

FIG. 1 shows one exemplary monitoring system 100 according to one preferred embodiment of the invention for monitoring use of the contents, such as medical pills, of a smart package 102, wherein the monitoring system 100 comprises not only a smart package but also database elements 104. The monitoring system may also comprise the smart package user's other terminal unit, such as a mobile communicator 105.

The smart package 102 comprises removable content units, such a pill type or tablet type objects, for example medical pills, as well as most preferably wireless communication elements 102a, which are most preferably implemented by means of a module. The module can be for example a GSM, GPRS or UMTS module capable of communicating with a base station included in a mobile communication system. Alternatively or additionally, the package may also feature a data transfer solution based on short range RF technology, such as RFFID or NFC technique, by way of which the package is able to communicate with some other RFIS, NFC or the like device 106. The package may also include a wired data transfer medium, such as a USB interface. According to one embodiment, the device 106 may be for example a device measuring the package user's physiological functions, from which the smart package can inquire measurement data for example in conjunction with the removal of a content unit and supply the database elements not only with information regarding the removal of a content unit but also information regarding the user's functions, such as for example heart rate information or other information, which it receives after inquiring from the device 106. It may also be the case that the sensors measuring physiological functions converse with the device 106 in a centralized manner, and the device 106 then delivers the information, which is has collected from the sensors, in an assembled form to the smart package as the latter inquires information.

It should particularly be noted that, according to one preferred embodiment, the backing comprises a docking unit 102b for docking said data transfer elements to the backing for example for the duration of medication package use, whereby, after the medication package use, the data transfer elements can be disengaged from the package for connecting the same for example to a new package, and the spent package can be recycled for example along with recyclable cardboard, or incinerated.

Figure 2:
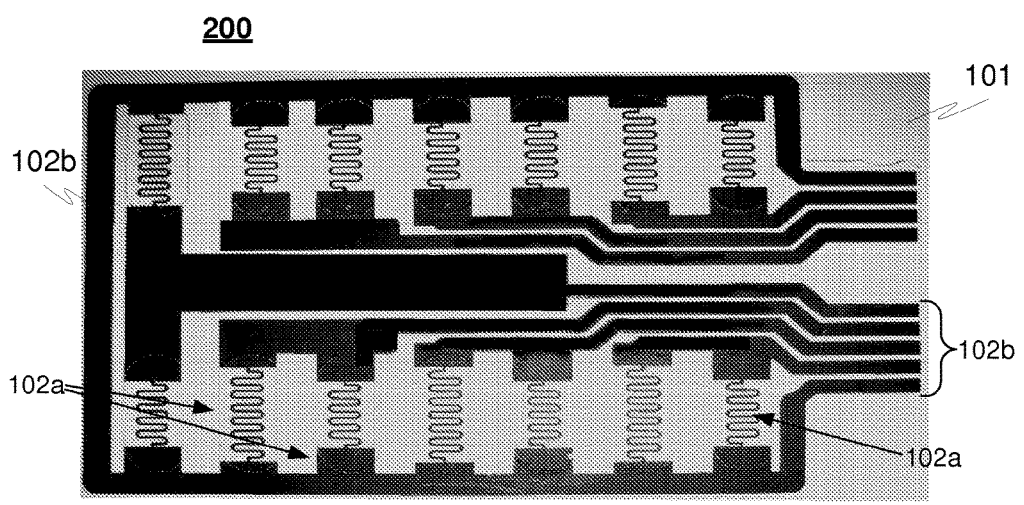
FIG. 2 shows, according to one preferred embodiment of the invention, one smart package of the monitoring arrangement.

The smart package (as shown in FIG. 2) is preferably adapted to detect said removal of a pill and to supply information to said database elements 104 by way of said communication elements 102a, 103, regarding a removal of said content unit. Said smart package can be identified by means of said database elements 104 on the basis of information it has delivered by way of said communication elements. The smart package may transmit for example a package identifying character string or, alternatively, its communication elements 102a may transmit specific identification data, such as the data of a SIM card, in connection with transmitting other information.

FIG. 2 shows one backing 200 for the smart package 102 of the monitoring system 100 according to one preferred embodiment of the invention, wherein the package is adapted to record a removal of pills by means of detection elements 102, 103 provided in the backing 200. The detection elements comprise electrical components 102a, 102b, which are most preferably pressed onto the backing 200 with methods of printing technology. The removal of a pill from the backing is adapted to bring about a structural change in at least one printed component, such that the change produces an electrically measurable change in at least one of said electrical components printed on the backing. The electrical printed component can be for example a resistor or a capacitor and said electrical change can be for example a change of resistance or capacitance. A component of the backing can be coupled to be a part of some electric circuit of the backing, such as an oscillator, whereby the change of resistance or capacitance brings about a change in the oscillator's frequency, the magnitude of which is proportional to the magnitude of the change in resistance or capacitance. Respectively, since every pill has a designated component, whose electrical property, such as resistance or capacitance, deviates from other components of the backing, the change-producing component, and thereby the pill corresponding to that component, can be identified on the basis of the magnitude of a change in resistance or capacitance or a change in the oscillator's frequency.

Described above are just a few embodiments for a solution of the invention. The principle according to the invention can naturally be varied within the scope of protection defined by the claims, for example in terms of implementation details as well as fields of use. The smart package of the invention is most preferably a fiber- or plastic based package. In some application examples, the fiber- or plastic based package material comprises cardboard. Alternatively, the fiber- or plastic-based package material may also comprise for example paper or the like. As an option to fiber, one embodiment of the invention enables using also plastics, polymer films, or the like. In reference to exemplary embodiments of the invention, it should indeed be noted that fiber or plastic may refer at least to the former and equivalents thereof. Hence, a functional backing can obtained by using almost any insulating and flat blank, fiber, fibrous mesh, textile, wallpaper, coating, biomaterial, ceramic coaster, glass, aluminum foil, etc. The backing 100 may be coated or uncoated, as well as wood-based or not wood-based. Thus, every substrate has its inherent benefits and drawbacks, which apply and are relevant to the required package. In terms of its temperature, the substrate can be for example such that the melting and reshaping point withstands temperatures of 200° C., temperatures particularly less than 250° C. or preferably less than 300° C. According to one embodiment, the smart package or the backing can be a blister package in itself, such as for example an aluminum foil coated with plastic or the like, upon which the components are pressed or printed for example by inkjet technique.

It should further be noted that the smart package used in the monitoring system of the invention can be for example a medication package, but also some other similar type package making use of a backing described in this document. This type of other smart packages can be for example racks and packages and shipping pallets intended for shipping and/or storing single-unit articles, such as yogurt containers or other one-by-one removable content units, whereby embodiments of the invention enable also carrying out inventory bookkeeping. The smart package of the invention, which is used for storage, for example a storage pallet or the like, may comprise a plurality of singly packed content units and may notify for example the accountant by way of the communication elements about a removal of content units, the number of such units, and that said smart package, i.e. in this case the storage pallet, is running out of such units.

According to one embodiment, the smart package or its backing can be for example a fiber-based layer, which is for example a bottom layer or part of it for a medication package or the like. According to one embodiment, the smart package is a blister package, wherein every blister comprises for example one medicine or dose of medicine, and wherein the blisters are arranged relative to the backing in such a way that each blister is matched by at least one printed electrical component set forth in this document. The removal of medicine is most preferably performed by pressing on the blister, whereby the medicine forces itself through the backing layer and at the same changes the structure of a corresponding component, such as for example breaks the component's electric circuit. According to another example, the smart package or its backing can be for example a backing of cardboard or made of some other appropriate material and intended for shipping and/or storing content units.

The invention claimed is:

1. A monitoring system for monitoring smart package content use, wherein the monitoring system comprises:
 a smart package of recyclable material, configured to comprise removable content units, a data transfer module functional in a cellular mobile communication network and a docking unit of recyclable material and comprising electrical conductor lines for docking said data transfer module to the smart package in releasable and electrical manner for the duration of package use such that the docking unit of the package accommodates said data transfer module, a module configured to receive positioning related location data and determine positioning of the smart package based on cellular information of the cellular mobile communication network, and database elements, and at least one sensor configured to measure a user's physiological function, wherein the smart package is adapted to detect said removal of a content unit and to supply information to said database elements by way of communication elements, involving electrical conductor lines of the docking unit and including said data transfer module docked at the smart package, regarding a removal of said content unit, the at least one sensor measures the user's physiological function based on an inquiry from the smart package in conjunction with said removal of the content unit, said smart package is capable of being identified by means of the database elements on the basis of information it has supplied by way of said communication elements, the network is configured to communicate with the data transfer module and/or the smart package via a base station, the smart package is, in addition to being configured to receive positioning related location data, further configured to gather sensing data including the measured user's physiological function, via the at least one sensor, and to transmit the sensing data to the database elements, and the monitoring system is configured to provision data regarding use of the smart package to a monitoring remote terminal based on the sensing data obtained from the smart package.

2. A monitoring system according to claim 1, wherein the smart package is provided for each content unit with a specific sensing element for detecting a removal of this particular content unit, the smart package being adapted to detect and identify, by means of said sensing elements, the removal of a specific content unit corresponding to the sensing device, and to supply information by means of communication elements, regarding the removal of just this particular content unit, and said each content unit being either a pill type or tablet type object.

3. A monitoring system according to claim 1, wherein the sensing element provided for a content unit comprises a component which is fabricated by methods of printing technology, the specific electrical values of at least two printed components present in the backing are adapted by methods of printing technology to be different from each other, such that the removal of a content unit brings about a change in the structure of a specific component, the removable content unit producing said change is adapted to be identified on the basis of a change in the specific electrical value inherent to said component, the component is a resistor, a capacitor, and/or a switch, and the specific electrical values is either a resistance or a capacitance.

4. A monitoring system according to claim 1, wherein the communication elements comprise wireless communication elements, wherein the smart package additionally comprises smart package identifying elements, the smart package identifying elements is a SIM card, and the wireless communication elements being a GSM, GPRS or UMTS module or a data transfer module functional in the cellular mobile communication network.

5. A monitoring system according to claim 1, wherein the database elements comprise linking means for linking the smart package identification information to the smart package user in the database elements, elements for linking a smart package content use instruction to said smart package identification information in the database elements, and communication elements for delivering content use relating instructions either to the smart package, to a mobile communicator, and/or to the user's other terminal unit, and the monitoring system comprises said terminal unit.

6. A monitoring system according to claim 5, wherein the database elements are adapted to deliver a reminder instruction for smart package content use in case of not having received information from the smart package regarding the smart package content use within a predetermined time frame.

7. A monitoring system according to claim 5 or 6, wherein the smart package comprises communication elements for receiving information from the database elements and an attention getter for producing a reminder to the user for smart package content use on the basis of instruction information received thereby from the database elements, and the attention getter being either a led component or a sound producing element.

8. A monitoring system according to claim 5, wherein the monitoring system is adapted to compare location data of both the smart package and the user's other terminal unit or the mobile communicator, and to produce an alarm in the event that said pieces of location data deviate from each other more than what has been prescribed, especially at a time when, according to the smart package content use instruction, some contents of the smart package should have been removed from said smart package.

9. A method for monitoring smart package content use, wherein a smart package comprises removable content units, wherein said removable content units being pill type or tablet type objects, wherein the method comprises:

providing the smart package comprising recyclable material with a data transfer module functional in a cellular mobile communication network and with a docking unit of recyclable material and comprising electrical conductor lines for docking said data transfer module to the smart package in releasable and electrical manner for the duration of package use such that the docking unit of the package accommodates said data transfer module, storing identification information in database elements, regarding said smart package, storing information in the database elements for using said smart package content according to which time intervals the content should be used as per instruction, linking said information regarding the smart package content use with said smart package identification information, and delivering information by way of communication elements, involving electrical conductor lines of the docking unit and including said data transfer module docked at the smart package, from said smart package to said database elements, regarding the removal of a content unit, said smart package being identifiable by the database elements on the basis of information it has supplied delivered by way of said communication elements,
wherein
the identification information being information about a SIM card included in the smart package,
the information being a medical prescription along with its dosage instructions and time attributes,
the network is configured to communicate with the data transfer module and/or the smart package via a base station,
the method further comprising determining positioning of the smart package based on cellular information of the cellular mobile communication network,
gathering sensing data, including a user's physiological function measured, via a sensor, and transmitting the sensing data to the database elements,
wherein the sensor measures the user's physiological function based on an inquiry from the smart package in conjunction with said removal of the content unit, and
provisioning data regarding use of the smart package to a monitoring remote terminal based on the sensing data obtained from the smart package.

10. A method according to claim 9, further comprising:
monitoring every removal of the smart package's content unit by means of a designated, identifiable sensing element, the smart package detecting and identifying, by means of said sensing elements, the removal of a specific content unit corresponding to a sensing element, and delivering information by way of communication elements, regarding the removal of just this particular content unit, wherein
the smart package's content unit being either a pill type or tablet type object.

11. A method according to claim 9, further comprising:
delivering instructions regarding content use from the database elements either to the smart package, his/her mobile communicator, and/or to the user's other terminal unit.

12. A method according to claim 9, further comprising:
delivering a reminder instruction from the database elements to the smart package, his/her mobile communicator, and/or to the user's other terminal unit, for using the smart package content in the event that the database elements have not received from the smart package information regarding smart package content use within a predetermined time frame.

13. A method according to claim 9, wherein
the smart package receives information from the database elements by way of communication elements and produces, by means of an attention getter, a reminder to the user for using the smart package content on the basis of instruction information it has received from the database elements, wherein
the attention getter being either a led component or a sound producing element.

14. A method according to claim 9, further comprising:
comparing pieces of location data regarding both the smart package and the user's other terminal unit or his/her mobile communicator, and producing an alarm in case said pieces of location data deviate from each other more than what has been prescribed, particularly at a time when, according to the smart package content use instruction, some content of the smart package should have been removed from said smart package.

15. A method for monitoring smart package content use, wherein a smart package comprises removable content units, wherein said removable content units being pill type or tablet type objects, wherein the method comprises:
providing the smart package comprising recyclable material with a data transfer module functional in a cellular mobile communication network and with a docking unit of recyclable material and comprising electrical conductor lines for docking said data transfer module to the smart package in releasable and electrical manner for the duration of package use such that the docking unit of the package accommodates said data transfer module,
storing identification information in database elements, regarding said smart package,
storing information in the database elements for using said smart package content according to which time intervals the content should be used as per instruction,
linking said information regarding the smart package content use with said smart package identification information, and
delivering information by way of communication elements, involving electrical conductor lines of the docking unit and including said data transfer module docked at the smart package, from said smart package to said database elements, regarding the removal of a content unit, said smart package being identifiable by the database elements on the basis of information it has supplied delivered by way of said communication elements,
wherein
the network is configured to communicate with the data transfer module and/or the smart package via a base station,
the method further comprising determining positioning of the smart package based on cellular information of the cellular mobile communication network,
gathering sensing data, including a user's physiological function, via a sensor, and transmitting the sensing data to the database elements,
wherein the sensor measures the user's physiological function based on an inquiry from the smart package in conjunction with said removal of the content unit, and
provisioning data regarding use of the smart package to a monitoring remote terminal based on the sensing data obtained from the smart package.

16. A method according to claim 15, wherein
the identification information being information about a SIM card included in the smart package.

17. A method according to claim 15, wherein
the information being a medical prescription along with its dosage instructions and time attributes.

18. A method according to claim 15, wherein
the identification information being information about a SIM card included in the smart package, and
the information being a medical prescription along with its dosage instructions and time attributes.

* * * * *